(12) United States Patent
Brückner et al.

(10) Patent No.: US 10,307,584 B2
(45) Date of Patent: Jun. 4, 2019

(54) BREAKER DEVICE FOR ACTING ONTO A CLOSURE ELEMENT OF A MEDICAL TUBING

(71) Applicant: Fresenius Kabi Deutschland GmbH, Bad Homburg (DE)

(72) Inventors: Thomas Brückner, Mömbris (DE); Christian Hennecke, Westerfeld (DE); Safet Jukovic, Frankfurt (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 15/758,924

(22) PCT Filed: Aug. 1, 2016

(86) PCT No.: PCT/EP2016/068264
§ 371 (c)(1),
(2) Date: Mar. 9, 2018

(87) PCT Pub. No.: WO2017/045826
PCT Pub. Date: Mar. 23, 2017

(65) Prior Publication Data
US 2018/0256884 A1    Sep. 13, 2018

(30) Foreign Application Priority Data

Sep. 14, 2015 (EP) ................................ EP15185036

(51) Int. Cl.
*F15B 13/01* (2006.01)
*A61M 39/22* (2006.01)
(Continued)

(52) U.S. Cl.
CPC ..... *A61M 39/221* (2013.01); *A61M 2039/087* (2013.01); *A61M 2039/222* (2013.01); *G05D 7/0617* (2013.01)

(58) Field of Classification Search
CPC .......... A61M 39/221; A61M 2039/087; A61M 2039/222; G05D 7/0617; B26F 3/00; B26F 3/002
(Continued)

(56) References Cited

U.S. PATENT DOCUMENTS 2,659,253 A    11/1953   Myrick
3,266,287 A    8/1966    Gill
(Continued)

FOREIGN PATENT DOCUMENTS

FR     2 968 568 A1    6/2012
WO    WO99/44652 A1   9/1999
(Continued)

OTHER PUBLICATIONS

European Search Report dated Mar. 4, 2014, for Application No. EP 13192157.9.
(Continued)

*Primary Examiner* — Minh Q Le
(74) *Attorney, Agent, or Firm* — Cook Alex Ltd.

(57) ABSTRACT

A breaker device for acting onto a closure element (40) of a medical tubing (4) comprises: a drive arrangement (2) having a drive device (20), a drive element (23) driven by the drive device (20) and at least one locking element (22A, 22B), and a breaker module (3) which is arrangeable on the drive arrangement (2). The breaker module (3) comprises a housing (30), a movable part (31) movably arranged on the housing (30), a breaking element (315) for acting onto the closure element (40) of the tubing (4) and a locking mechanism (32A, 32B). The breaker module (3) in an attached state is placed on the drive arrangement (2) and is locked to the drive arrangement (2) via the locking mechanism (32A, 32B) engaging with the at least one locking element (22A, 22B), the drive element (23) being in operative connection
(Continued)

with the movable part (31) in the attached state such that a movement of the drive element (23) causes the movable part (31) to move for actuating the breaking element (315). The breaker module (3) is releasable from the drive arrangement (2) by disengaging the locking mechanism (32A, 32B) from the at least one locking element (22A, 22B). Herein, the locking mechanism comprises at least one actuation member (32A, 32B) which is displaceable between a first position and a second position with respect to the housing (30), wherein the at least one actuation member (32A, 32B) is constituted to act, in the first position, onto the movable part (31) to force the movable part (31) into a position in which the movable part (31) can be brought into operative connection with the drive element (20) when arranging the breaker module (3) on the drive arrangement (2), and to engage, in the second position, with the at least one locking element (22A, 22B) of the drive arrangement (2) when the breaker module (3) is in the attached state.

20 Claims, 2 Drawing Sheets

(51) Int. Cl.
*A61M 39/08* (2006.01)
*G05D 7/06* (2006.01)

(58) Field of Classification Search
USPC .......... 137/487.5, 68.11, 269; 251/349, 342; 225/103; 604/167.01, 403
See application file for complete search history.

(56) References Cited

U.S. PATENT DOCUMENTS

| | | | |
|---|---|---|---|
| 4,181,140 A | 1/1980 | Bayham et al. | |
| 4,294,247 A | 10/1981 | Carter et al. | |
| 4,340,049 A | 7/1982 | Munsch | |
| 4,386,622 A | 6/1983 | Munsch | |
| 4,417,679 A * | 11/1983 | Shields | B26F 3/002 225/93 |
| 4,510,825 A | 4/1985 | Neron et al. | |
| 4,586,928 A | 5/1986 | Barnes et al. | |
| 4,720,032 A * | 1/1988 | LaBounty | B23D 17/06 104/7.1 |
| 4,805,821 A * | 2/1989 | Kowalczyk | B26F 3/002 225/103 |
| 5,427,145 A | 6/1995 | Grabenkort | |
| 5,709,685 A | 1/1998 | Dombrowski et al. | |
| 5,824,216 A | 10/1998 | Joie et al. | |
| 5,826,621 A * | 10/1998 | Jemmott | A61M 5/16831 137/853 |
| 5,884,847 A * | 3/1999 | Christopher | A62C 31/05 239/390 |
| 6,132,413 A | 10/2000 | Mathias et al. | |
| 6,156,025 A | 12/2000 | Niedospial, Jr. et al. | |
| 6,398,134 B1 * | 6/2002 | Hickson | B05B 1/16 239/394 |
| 6,409,032 B1 | 6/2002 | Bekkers et al. | |
| 6,427,893 B1 | 8/2002 | Penrod et al. | |
| 6,470,780 B1 | 10/2002 | Benuzzi | |
| 6,988,677 B2 * | 1/2006 | Sodemann | B08B 3/026 239/525 |
| 9,192,756 B2 | 11/2015 | Deverre et al. | |
| 2001/0039404 A1 | 11/2001 | Rolle | |
| 2003/0167893 A1 | 9/2003 | Morris et al. | |
| 2006/0022455 A1 * | 2/2006 | Mieger | B60D 1/62 285/124.5 |
| 2009/0227961 A1 | 9/2009 | Meisberger et al. | |
| 2010/0132512 A1 | 6/2010 | Bucciaglia et al. | |
| 2010/0269584 A1 | 10/2010 | Horst | |
| 2011/0198350 A1 | 8/2011 | Meisberger et al. | |
| 2012/0010569 A1 * | 1/2012 | Parihar | A61B 17/3421 604/167.01 |
| 2013/0340836 A1 | 12/2013 | Wambold | |
| 2015/0306371 A1 * | 10/2015 | Salo | A61M 39/221 225/1 |
| 2015/0367120 A1 * | 12/2015 | Kusters | A61M 39/08 137/15.09 |

FOREIGN PATENT DOCUMENTS

| | | |
|---|---|---|
| WO | WO2004/058046 A2 | 7/2004 |
| WO | WO2006/114319 A1 | 11/2006 |
| WO | WO2010/065396 A1 | 6/2010 |
| WO | WO2012/080664 A2 | 6/2012 |
| WO | WO2012080664 A2 | 6/2012 |
| WO | WO2012/177158 A1 | 12/2012 |
| WO | WO2014/083412 A1 | 6/2014 |
| WO | WO2015/113701 A1 | 8/2015 |

OTHER PUBLICATIONS

International Search Report and Written Opinion, counterpart International Appl. No. PCT/EP2016/068264, dated May 10, 2016 (8 pages).
YouTube video—https://www.youtube.com/watch?v=7u677isN1Og, published on Jul. 26, 2012, cited in U.S. Appl. No. 13/833,990 in Supplemental Information Disclosure Statement filed Jul. 8, 2016. A DVD was provided and assigned Artifact No. 13833990UA.

* cited by examiner

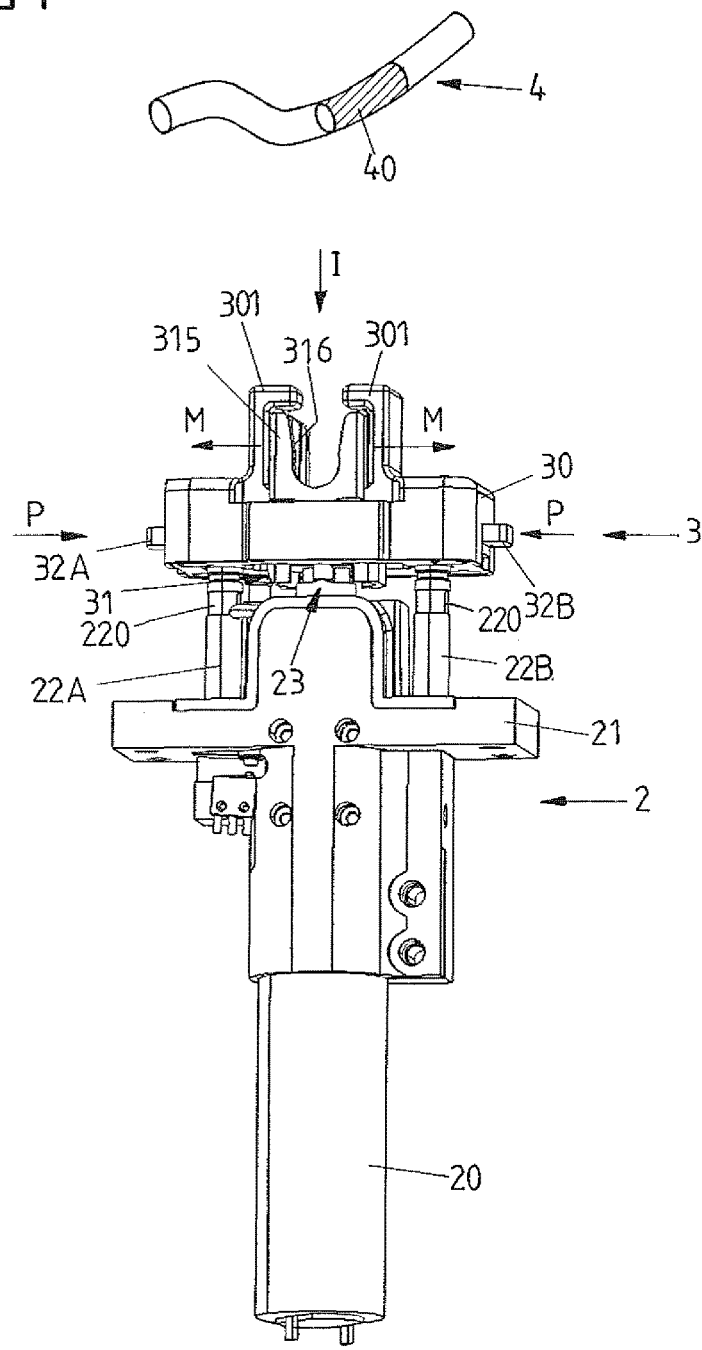

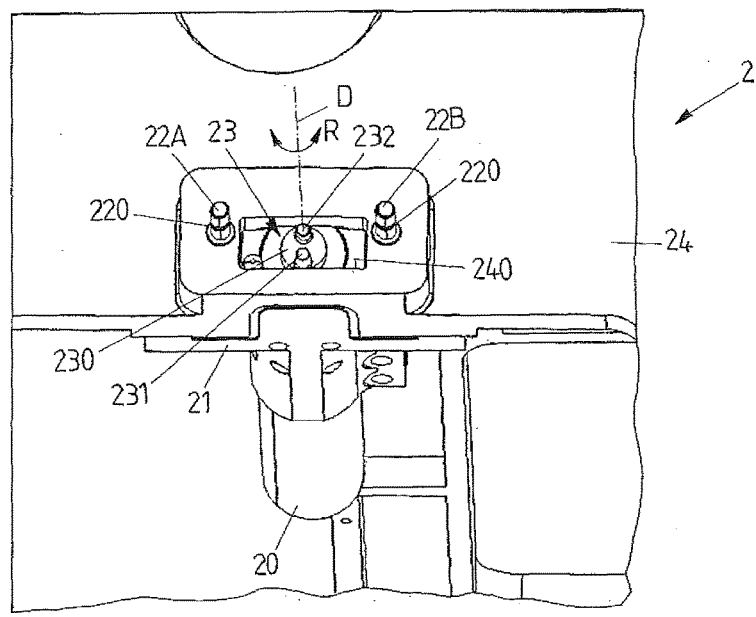
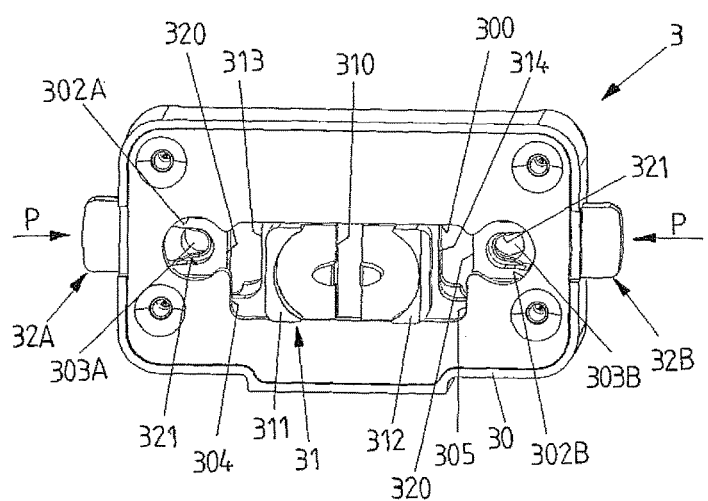

BREAKER DEVICE FOR ACTING ONTO A CLOSURE ELEMENT OF A MEDICAL TUBING

The invention relates to a breaker device for acting onto a closure element of a medical tubing according to the preamble of claim 1.

A breaker device of this kind, commonly referred to also as "breaking device" or "breaker", comprises a drive arrangement and a breaker module arrangeable on the drive arrangement. The drive arrangement comprises a drive device, a drive element driven by the drive device and at least one locking element. The breaker module comprises a housing, a movable part movably arranged on the housing, a breaking element for acting onto the closure element of the tubing and a locking mechanism. In an attached state the breaker module is placed on the drive arrangement and is locked to the drive arrangement via the locking mechanism engaging with the at least one locking element. In this attached state the drive element is in operative connection with the movable part such that a movement of the drive element causes the movable part to move for actuating the breaking element.

The breaker module hence, in a modular fashion, can be arranged on the drive arrangement and, when it is attached to the drive arrangement, is functionally connected to the drive arrangement such that, via the drive device and the drive element of the drive arrangement, the movable part of the breaker module can be driven for actuating the breaking element. Via the breaking element a closure element of a medical tubing arranged on the breaker module can be opened such that a flow through the medical tubing becomes possible.

In medical tubing sets, for example within a blood bag system comprising one or multiple blood bags or other liquid containers, closure elements are placed within tubing sections in order to close a flowpath through the corresponding tubing. By closing one or multiple tubing sections of a tubing set, a blood bag system can for example be stored or transported. In order to prepare a blood component, for example for infusion purposes, a flowpath through a tubing from one container to another may then be opened by acting onto the closure element within the tubing.

Different systems of closure elements exist for closing a tubing and, hence, preventing a flow through the tubing. Closure elements generally have the shape of a cap or pin which is inserted into the lumen of a tubing such that the lumen of the tubing is closed off and a flow through the tubing is prevented. The different existing systems herein differ in the way the closure elements can be opened in order to allow a flow through the tubing.

In a first system, as for example described in WO 2004/058046 A2 or WO 2012/080664 A2, an opening of a flowpath can be achieved by breaking the closure element. In another system, as described for example in WO 2006/114319 A1, an opening of a flowpath can be achieved by deforming the closure element without actually breaking it. In both cases, the closure element even after opening remains in the tubing, but is broken or deformed such that a flow through the tubing is no longer prevented.

In principle, the opening of a closure element of this kind can be achieved manually by manually breaking or deforming the closure element within the tubing. For example, a closure element as described in WO 2012/080664 A2 can be broken by manually grabbing a tubing at the location of the closure element and by repeatedly bending it until the closure element breaks.

However, this may be a tedious task for a user such that there is a desire to provide an automatic opening device which can automatically open a closure element within a tubing.

Herein, because different systems of closure elements exist, one opening device may not be suitable to open different kinds of closure elements, because the different closure elements may require a different opening action. This may make it necessary to provide different opening devices for different closure elements, which however is costly and therefore to be avoided.

Instead of using multiple different opening devices, a breaker device of the type concerned herein may be used together with different breaker modules, the breaker modules having different configurations such that they are suitable to be used in connection with different closure elements, as for example described in WO 2014/083412 A1.

For this, the breaker module is releasable from the drive arrangement by disengaging the locking mechanism of the breaker module from the at least one locking element of the drive arrangement, such that one breaker module can be replaced by another.

For placing the breaker module on the drive arrangement, on the one hand the locking mechanism of the breaker module is to be brought into engagement with the at least one locking element of the drive arrangement. On the other hand the movable part of the breaker module must be coupled to the drive element of the drive arrangement such that, when the breaker module is attached to the drive arrangement, the movable part can be driven by the drive element of the drive arrangement.

Currently, when placing a breaker module on a drive arrangement, care must be taken that the movable part is in a position in which it can be coupled to the drive element of the drive arrangement. If this is ensured, the breaker module can be placed on the drive arrangement, and the locking can be established by actuating the locking mechanism to engage with one or multiple locking elements of the drive arrangement. For example, the locking can be established via screws or a quick locking mechanism. In turn, for removing a breaker module from a drive arrangement, the locking must be released for example by releasing a screw connection or by unlocking a quick locking mechanism.

It is an object of the instant invention to provide a breaker device which in an easy, releasable fashion allows to place a breaker module on a drive arrangement.

This object is achieved by means of a breaker module comprising the features of claim 1.

Accordingly, the locking mechanism comprises at least one actuation member which is displaceable between a first position and a second position with respect to the housing. Herein, the at least one actuation member is constituted to act, in the first position, onto the movable part to force the movable part into a position in which the movable part can be brought into operative connection with the drive element when arranging the breaker module on the drive arrangement, and to engage, in the second position, with the at least one locking element of the drive arrangement when the breaker module is in the attached state.

Accordingly, the locking mechanism of the breaker module comprises one or multiple actuation members which are arranged on the housing and which can be displaced relative to the housing. These actuation members are constituted to both act onto the movable part and to engage with the locking elements of the drive arrangement.

In particular, in the first position the actuation member acts onto the movable part to force the movable part into a position in which the movable part can be brought into operative connection with the drive element when arranging the breaker module on the drive arrangement. Hence, when the actuation member is brought into its first position, the movable part is held in a predefined position by means of the actuation member such that the movable part can come into a coupling engagement with the drive element of the drive arrangement when the breaker module is placed on the drive arrangement.

In this way no particular care must be taken to bring the movable part into a particular position when placing the breaker module on the drive arrangement. This is done via the actuation member, which forces the movable part into the predefined position in which the coupling can be established.

In the first position the at least one actuation member preferably is in a position in which the locking engagement with the at least one locking element of the drive arrangement can be established. When the at least one actuation member is in the first position the breaker module hence can be placed on the drive arrangement for establishing the locking.

In the second position, in turn, the at least one actuation member engages with the at least one locking element of the drive arrangement when the breaker module is in the attached state. Hence, when the breaker module is arranged on the drive arrangement and the actuation member is brought into the second position, the locking engagement between the actuation member and the locking element of the drive arrangement is established such that the breaker module is locked relative to the drive arrangement and thus is held in position on the drive arrangement.

For displacing the at least one actuation member towards the first position, the at least one actuation member may, in one embodiment, be pushed in a pushing direction into the housing. Hence, for bringing the at least one actuation member into the first position, a user pushes onto the actuation member.

In one embodiment, the at least one actuation member is pretensioned with respect to the housing in a direction pointing towards the second position. Hence, the actuation member in a default state assumes the second position towards which it is moved when no user acts onto the actuation member. If a user pushes onto the actuation member to bring the actuation member into the first position, and afterwards releases the actuation member, the actuation member will automatically revert to the second position without a further user interaction.

In one embodiment, the at least one actuation member comprises an engagement opening through which the at least one locking member reaches in the attached state. The engagement opening may be shaped such that the locking member can be inserted into the engagement opening when the actuation member is in the first position. When the actuation member then assumes its second position, an engagement between the actuation member and the locking element is established such that the breaker module is locked relative to the drive arrangement.

In one embodiment, the breaker module comprises two actuation members which are arranged on the housing such that they can be displaced along opposite directions. In particular, the two actuation members may be pushed into the housing towards each other for bringing the two actuation members into their respective first position. In turn, when the actuation members revert to their second position, they may move in opposite directions away from one another to establish the locking with corresponding locking elements of the drive arrangement.

In another aspect, the drive element is rotatable about an axis of rotation. The drive element may for example be rotatable with respect to a housing of the drive arrangement and is driven by the drive device of the drive arrangement to rotate about an axis of rotation. The drive device may for example be an electric motor, wherein it is also conceivable that the drive device is implemented by a manual drive.

The drive element may for example comprise one or multiple coupling elements to establish a positive-locking coupling with the movable part. The coupling element may for example be constituted by a pin protruding along the axis of rotation from a rotating body of the drive element. The pin herein beneficially is arranged eccentrically to the axis of rotation of the drive element such that it moves along a circular path about the axis of rotation when the drive element is rotated.

The coupling element of the drive element engages with a corresponding coupling mechanism of the movable part when the breaker module is arranged on the drive arrangement. The coupling mechanism of the movable part may for example be constituted by a groove or another engagement means into which the coupling element of the drive element may reach such that a movement of the drive element is transferred into a suitable movement of the movable part.

The movable part is coupled to the breaking element and, when moved, moves the breaking element such that the breaking element may perform a breaking motion for opening a closure element of a medical tubing arranged on the breaking element. The breaking element may for example have the shape of a fork into which the medical tubing may be inserted.

The movable part may for example be longitudinally guided on the housing such that, when driven by the drive element, the movable part is displaced with respect to the housing along a longitudinal movement direction. It is to be understood, however, that different breaker modules may have different movable parts which may perform a different kind of movement.

The idea underlying the invention shall subsequently be described in more detail with respect to the embodiments shown in the figures. Herein:

FIG. 1 shows a perspective view of a drive arrangement of a breaker device together with a breaker module;

FIG. 2 shows a top view of the drive arrangement; and

FIG. 3 shows a view of the breaker module from beneath.

FIG. 1 shows a breaker device 1 having a drive arrangement 2 and a breaker module 3.

The drive arrangement 2 comprises an electric drive device 20 in the shape of an electric motor and a drive element 23 which, as visible in FIG. 2, is rotatable about a rotational axis D and comprises a rotating body 230 having a cylindrical shape and a pair of coupling elements 231, 232 in the shape of pins protruding from the body 230 along the axis of rotation D. The pins 231, 232 are arranged eccentrically to the axis of rotation D such that the pins 231, 232 move along a circular path along a rotation direction R about the axis of rotation D when the drive element 23 is driven by means of the electric drive device 20.

The drive arrangement 2 furthermore comprises a mounting element 21 on which the electric drive device 20 is mounted. Via the mounting element 21 the electric drive device 20 is connected to a housing element 24, as shown in FIG. 2.

The breaker device 1 may be part of a larger system such as a pump device, a centrifugation device or the like, the housing element 24 being part of the overall housing of the system.

As visible from FIGS. 1 and 2, a pair of locking elements 22A, 22B are arranged on the mounting element 21 and protrude from the mounting element 21 along the axis of rotation D. The locking elements 22A, 22B reach through the housing element 24 such that they are accessible from the outside, as visible in FIG. 2.

The locking elements 22A, 22B have the shape of pins and each comprise a circular groove 220. The locking elements 22A, 22B serve to establish a locking between the drive arrangement 2 and a breaker module 3 attached to the drive arrangement 2, as shall be described further below.

The drive element 23 is placed within an opening 240 of the housing element 24 such that it also is accessible from the outside. Via the drive element 23 an operative connection is established between a movable part 31 of the breaker module 3 and the electric drive device 20, as it also shall be described further below.

The breaker module 3, as shown in FIG. 3, comprises a housing 30 having a longitudinal opening 300 at a bottom face facing the drive arrangement 2 when placing the breaker module 3 on the drive arrangement 2. Within the opening 300 the movable part 31 is placed such that the movable part 31 is guided on the housing 30 along a longitudinal movement direction.

The breaker module 3 furthermore comprises two actuation members 32A, 32B which are arranged on the housing 30 such that they can be displaced with respect to the housing 30 along a pushing direction P between a first, inner position and a second, outer position. The actuation members 32A, 32B have the shape of buttons and can be pushed into the housing 30 manually by a user by pressing onto the actuation members 32A, 32B.

The actuation members 32A, 32B are, in one embodiment, pretensioned towards their outer, second position such that, when released, they will assume there second, outer position (shown in FIG. 3).

The actuation members 32A, 32B serve a twofold function.

The actuation members 32A, 32B each comprise a head section 320, by which they can be brought into engagement with a corresponding engagement section 313, 314 in the shape of a recess on the movable part 31. Hence, when pushing the actuation members 32A, 32B in the pushing direction P into the housing 30, the head sections 320 engage with the engagement sections 313, 314 on opposite ends of the movable part 31 and in this way force the movable part 31 into a predefined, central position within the opening 300 of the housing 30. Hence, by pushing onto the actuation members 32A, 32B the movable part 31 is brought into a predefined position in which it can be coupled with the drive element 23 when the breaker module 3 is arranged on the drive arrangement 2.

For establishing the coupling with the drive arrangement 2 the movable part 31 comprises a groove 310 in which the pin 231 of the drive element 23 (which has a larger height than the other pin 232) can engage. When placing the breaker module 3 on the drive arrangement 2 by approaching the drive arrangement 2 in an insertion direction I (see FIG. 1), the pin 231 is introduced into the groove 310 which is easily possible if the movable part 31 is held in a predefined, central position by means of the actuation members 32A, 32B (assuming that the drive element 23 assumes a default position when no breaker module 3 is arranged on the drive arrangement 2). The coupling between the drive element 23 and the movable part 31 of the breaker module 3 hence can easily be established by holding the movable part 31 in a predefined, central position by means of the actuation members 32A, 32B.

When placing the breaker module 3 on the drive arrangement 2, the breaker module 3 is approached towards the locking elements 22A, 22B arranged on the mounting element 21 of the drive arrangement 2, and the locking elements 22A, 22B are inserted into openings 302A, 302B on the bottom face of the housing 30 and are introduced into openings 303A, 303B inside the housing 30 through engagement openings 321 of the actuation members 32A, 32B. If the actuation members 32A, 32B are in their first, inner position when placing the breaker module 3 on the drive arrangement 2, the openings 303A, 303B inside the housing 30 are accessible such that the locking elements 22A, 22B may be inserted into such openings 303A, 303B.

Once the breaker module 3 is placed on the drive arrangement 2, the actuation members 32A, 32B are released such that, due to the pretensioning force of spring elements acting between the actuation members 32A, 32B and the housing 30, they are reverted to their second position in a direction opposite the respective pushing direction P. By this a rim extending (half-way) around the engagement opening 321 of each actuation member 32A, 32B engages with the groove 220 of the corresponding locking element 22A, 22B, such that the breaker module 3 is mechanically locked to the locking elements 22A, 22B. In particular, the breaker module 3 in this way is held on the drive arrangement 2 and cannot be removed, at least not without releasing the locking, from the drive arrangement 2.

If a tubing 4 shall be opened by acting onto a closure element 40 placed within the tubing 4, the tubing 4 is inserted into the insertion direction I into a space between housing elements 301 on the housing 30 and is introduced into the reception opening 316 of the breaking element 315. During operation the drive element 23 is then rotated and moves within a space confined between protrusions 311, 312 on the movable part 31. Due to the engagement of the pin 231 with the groove 310 the movable part 31 is forced by the rotating movement of the drive element 23 into a longitudinal back and forth movement within the opening 300 of the housing 30, which is transferred to the breaking element 315 such that the breaking element 315 moves for example along a movement direction M and by this acts onto the tubing 4 placed in the reception opening 316 of the fork-shaped breaking element 315.

If the breaker module 3 shall be replaced by another breaker module 3 for acting onto a different tubing 4 comprising a different closure element 40 of a different kind, a user presses onto the actuation members 32A, 32B and by this releases the mechanical locking of the actuation members 32A, 32B and the locking elements 22A, 22B. The breaker module 3 hence may be removed from the locking elements 22A, 22B in a direction opposite to the insertion direction I, and another breaker module 3 may be placed on the drive arrangement 2.

Different breaker modules 3 may comprise different movable parts 31 performing different motions. In each case, herein, a rotating movement of the drive element 23 is transferred to a corresponding movable part 31 of a breaker module 3 and by this a breaking element 315 of the breaker module 3 is driven to act onto a closure element 40 of a tubing 4 inserted into a reception opening 316 of the breaking element 315.

The invention is not limited to the embodiments described above, but may be implemented in an entirely different fashion.

In particular, the breaker module may have a different shape and function. For example, the movable part may perform a rotating movement or the like.

The breaking element of the breaker module may be fixedly connected to the movable part such that the breaking element performs the same movement as the movable part. However, it is also conceivable that the breaking element is connected to the movable part via a suitable gearing such that the movement of the movable part is transferred into a different movement of the breaking element.

LIST OF REFERENCE NUMERALS

1 Breaker device
2 Drive arrangement (backend)
20 Electric drive device
21 Mounting element
22A, 22B Lock element
220 Groove
23 Drive element
230 Body
231, 232 Pin
24 Housing element
240 Opening
3 Breaker module
30 Housing
300 Guide opening
301 Housing elements
302A, 302B Opening
303A, 303B Opening
31 Movable part
310 Groove
311, 312 Protrusion element
313, 314 Engagement section
315 Breaking element
316 Reception opening
32A, 32B Actuation member (button)
320 Head section
321 Engagement opening
4 Tubing
40 Closure element
D Axis of rotation
I Insertion direction
M Movement direction
P Pushing direction
R Rotation direction

The invention claimed is:

1. A breaker device for acting onto a closure element of a medical tubing, comprising:
a drive arrangement having a drive device, a drive element driven by the drive device and at least one locking element, and
a breaker module which is arrangeable on the drive arrangement, the breaker module comprising a housing, a movable part movably arranged on the housing, a breaking element for acting onto the closure element of the tubing and a locking mechanism, wherein the breaker module in an attached state is placed on the drive arrangement and is locked to the drive arrangement via the locking mechanism engaging with the at least one locking element, the drive element being in operative connection with the movable part in the attached state such that a movement of the drive element causes the movable part to move for actuating the breaking element, wherein the breaker module is releasable from the drive arrangement by disengaging the locking mechanism from the at least one locking element, the locking mechanism further comprising at least one actuation member which is displaceable between a first position and a second position with respect to the housing, wherein the at least one actuation member is constituted to act, in the first position, onto the movable part to force the movable part into a position in which the movable part can be brought into operative connection with the drive element when arranging the breaker module on the drive arrangement, and to engage, in the second position, with the at least one locking element of the drive arrangement when the breaker module is in the attached state.

2. The breaker device according to claim 1, wherein the at least one actuation member is pushed in a pushing direction into the housing to displace the at least one actuation member towards the first position.

3. The breaker device according to claim 1, wherein the at least one actuation member is pretensioned with respect to the housing in a direction pointing towards the second position.

4. The breaker device according to claim 1 wherein the at least one actuation member comprises an engagement opening through which the at least one locking member reaches in the attached state.

5. The breaker device according to claim 1 wherein the at least one actuation member comprises a head section facing an engagement section of the movable part, the head section engaging with the engagement section in the first position of the at least one actuation member.

6. The breaker device according to claim 1 further comprising two actuation members arranged displaceably on the housing along opposite directions.

7. The breaker device according to claim 1 wherein the drive element is rotatable about an axis of rotation.

8. The breaker device according to claim 1 wherein the drive element comprises at least one coupling element to establish a positive-locking coupling with the movable part in the attached state.

9. The breaker device according to claim 1 wherein the movable part is guided on the housing such that the movable part is displaceable with respect to the housing along a longitudinal movement direction.

10. The breaker device according to claim 2 wherein the at least one actuation member is pretensioned with respect to the housing in a direction pointing towards the second position.

11. The breaker device according to claim 2 wherein the at least one actuation member comprises an engagement opening through which the at least one locking member reaches in the attached state.

12. The breaker device according to claim 3 wherein the at least one actuation member comprises an engagement opening through which the at least one locking member reaches in the attached state.

13. The breaker device according to claim 2 wherein the at least one actuation member comprises a head section facing an engagement section of the movable part, the head section engaging with the engagement section in the first position of the at least one actuation member.

14. The breaker device according to claim 3 wherein the at least one actuation member comprises a head section facing an engagement section of the movable part, the head section engaging with the engagement section in the first position of the at least one actuation member.

15. The breaker device according to claim 4 wherein the at least one actuation member comprises a head section facing an engagement section of the movable part, the head section engaging with the engagement section in the first position of the at least one actuation member.

16. The breaker device according to claim 2 further comprising two actuation members are arranged displaceably on the housing along opposite directions.

17. The breaker device according to claim 3 further comprising two actuation members are arranged displaceably on the housing along opposite directions.

18. The breaker device according to claim 4 further comprising two actuation members are arranged displaceably on the housing along opposite directions.

19. The breaker device according to claim 5 further comprising two actuation members are arranged displaceable on the housing along opposite directions.

20. The breaker device according to claim 2 wherein the drive element is rotatable about an axis of rotation.

* * * * *